US010022083B2

(12) United States Patent
Al-Terki

(10) Patent No.: US 10,022,083 B2
(45) Date of Patent: Jul. 17, 2018

(54) MULTIPLE ORAL AND NASAL SURGICAL PROCEDURES METHOD AND KIT

(71) Applicant: Abdulmohsen E. A. H. Al-Terki, Mishref (KW)

(72) Inventor: Abdulmohsen E. A. H. Al-Terki, Mishref (KW)

( * ) Notice: Subject to any disclaimer, the term of this patent is extended or adjusted under 35 U.S.C. 154(b) by 1031 days.

(21) Appl. No.: 13/784,719

(22) Filed: Mar. 4, 2013

(65) Prior Publication Data

US 2013/0178763 A1    Jul. 11, 2013

Related U.S. Application Data

(63) Continuation-in-part of application No. 13/474,590, filed on May 17, 2012, now Pat. No. 8,387,798, and
(Continued)

(51) Int. Cl.
*A61B 5/00*        (2006.01)
*A61B 5/103*       (2006.01)
(Continued)

(52) U.S. Cl.
CPC ............ *A61B 5/4818* (2013.01); *A61B 1/233* (2013.01); *A61B 5/103* (2013.01); *A61B 5/4836* (2013.01);
(Continued)

(58) Field of Classification Search
CPC ..... A61B 5/4818; A61B 5/103; A61B 5/4836; A61B 5/566; A61B 1/233; A61B 6/03;
(Continued)

(56) References Cited

U.S. PATENT DOCUMENTS 4,825,545 A    5/1989 Chase et al.
5,230,356 A    7/1993 Villas
(Continued)

FOREIGN PATENT DOCUMENTS

JP       2009284956 A * 12/2009 ............... A61B 1/00
WO   WO 2010/126912      11/2010

OTHER PUBLICATIONS

Richadson et al., Protocol for the Examination of Specimens from Patients with Carcinomas of the Lip and Oral Cavity, Based on AJCC/UICC TNM, 7th edition, Protocol web posting date: Oct. 2009.*
(Continued)

*Primary Examiner* — Bo J Peng
(74) *Attorney, Agent, or Firm* — Richard C. Litman

(57) ABSTRACT

The method of performing multiple oral and nasal surgical procedures in the head and neck region provides a systematic procedure for the performance of multiple operations for correcting various ear, nose, and throat conditions that cause snoring and obstructive sleep apnea (OSA) in the patient. The method allows the surgeon to perform multiple operating procedures in the nose, mouth, and/or throat in a single operating session, due to the use of hemostatic sheet and gel treatments in lieu of suturing and post-operative nasal hemostatic packs that preclude nasal breathing. The various surgical implement kits allow the surgeon to select the appropriate kit according to the procedure(s) to be performed. The procedure(s) is/are selected in accordance with a specific customized treatment plan that is developed by the surgeon for the individual patient, which other surgeons involved in snoring or OSA surgery can comprehend.

5 Claims, 11 Drawing Sheets

Related U.S. Application Data a continuation-in-part of application No. 13/152,048, filed on Jun. 2, 2011.

(51) Int. Cl.

| | | |
|---|---|---|
| *A61B 1/233* | (2006.01) | |
| *A61B 6/03* | (2006.01) | |
| *A61B 17/3211* | (2006.01) | |
| *A61B 17/34* | (2006.01) | |
| *A61F 5/56* | (2006.01) | |
| *A61B 17/12* | (2006.01) | |
| *A61B 17/24* | (2006.01) | |
| *A61B 50/30* | (2016.01) | |

(52) U.S. Cl.
CPC ............ *A61B 6/03* (2013.01); *A61B 17/3211* (2013.01); *A61B 17/34* (2013.01); *A61B 50/30* (2016.02); *A61B 2017/12004* (2013.01); *A61B 2017/248* (2013.01); *A61F 5/566* (2013.01)

(58) Field of Classification Search
CPC ..... A61B 17/3211; A61B 17/34; A61B 50/30; A61B 2017/12004; A61B 2017/248
See application file for complete search history.

(56) References Cited

U.S. PATENT DOCUMENTS

| | | | |
|---|---|---|---|
| 5,254,128 | A | 10/1993 | Mesa |
| D390,659 | S | 2/1998 | Chan |
| 5,773,033 | A | 6/1998 | Cochrum et al. |
| 5,843,107 | A | 12/1998 | Landis et al. |
| 5,915,433 | A | 6/1999 | Hybler |
| 6,001,113 | A | 12/1999 | Goldblum |
| 6,206,192 | B1 | 3/2001 | Winstead et al. |
| 6,393,404 | B2 | 5/2002 | Waters et al. |
| 6,475,172 | B1 | 11/2002 | Hall |
| 6,494,868 | B2 | 12/2002 | Amar |
| 6,509,028 | B2 | 1/2003 | Williams et al. |
| 6,559,803 | B2 | 9/2003 | Ashman |
| 6,634,503 | B2 | 10/2003 | Welsh, Jr. |
| 6,699,940 | B2 | 3/2004 | Shalaby |
| 6,933,326 | B1 | 8/2005 | Griffey et al. |
| 7,303,759 | B2 | 12/2007 | Mershon |
| D595,963 | S | 7/2009 | Gronikowski |
| 7,842,041 | B2 | 11/2010 | Liu et al. |
| 7,951,155 | B2 | 5/2011 | Smedley et al. |
| 8,088,093 | B2 | 1/2012 | Ottuso et al. |
| 2002/0165462 | A1* | 11/2002 | Westbrook et al. .......... 600/529 |
| 2003/0187381 | A1 | 10/2003 | Greenawalt et al. |
| 2003/0224000 | A1 | 12/2003 | Kokai-Kun et al. |
| 2005/0234313 | A1* | 10/2005 | Rowlandson et al. ........ 600/301 |
| 2005/0234439 | A1* | 10/2005 | Underwood .................... 606/32 |
| 2005/0240147 | A1* | 10/2005 | Makower et al. ......... 604/96.01 |
| 2005/0261625 | A1 | 11/2005 | Ashman |
| 2006/0112959 | A1* | 6/2006 | Mechlenburg et al. . 128/204.21 |
| 2007/0038298 | A1 | 2/2007 | Sulner et al. |
| 2007/0136097 | A1 | 6/2007 | Demers et al. |
| 2007/0239056 | A1* | 10/2007 | Moore ......................... 600/529 |
| 2007/0264310 | A1 | 11/2007 | Hissong et al. |
| 2008/0027480 | A1* | 1/2008 | van der Burg et al. ...... 606/199 |
| 2008/0044848 | A1 | 2/2008 | Heidaran |
| 2008/0097391 | A1 | 4/2008 | Feinberg et al. |
| 2009/0068155 | A1 | 3/2009 | Frey, II et al. |
| 2009/0131950 | A1 | 5/2009 | Liu et al. |
| 2009/0270835 | A1 | 10/2009 | Kushner |
| 2010/0036308 | A1 | 2/2010 | Ottuso et al. |
| 2010/0057047 | A1 | 3/2010 | Djupesland et al. |
| 2010/0121284 | A1 | 5/2010 | Hexsel |
| 2010/0215591 | A1 | 8/2010 | Stone et al. |
| 2011/0172704 | A1 | 7/2011 | Bleier et al. |
| 2011/0238431 | A1 | 9/2011 | Cionni et al. |
| 2011/0295083 | A1* | 12/2011 | Doelling et al. .............. 600/301 |
| 2011/0311588 | A1 | 12/2011 | Comans |
| 2012/0296675 | A1 | 11/2012 | Silverman |

OTHER PUBLICATIONS

Zucconi et al., Habitual snoring with and without obstructive sleep apnoea: the importance of cephalometric variables, Thorax 1992 47: 157-161.*

Chan et al., Obstructive Sleep Apnea in Children, Am Fam Physician 2004;69:1147-54,1159-60.*

Cahali et al., Tonsil volume, tonsil grade and obstructive sleep apnea: is there any meaningful correlation?, CLINICS 2011;66,8:1347-1351.*

Injury Severity Scoring, http://www.surgicalcriticalcare.net/Resources/injury_severity_scoring.pdf, p. 1-12, May 29, 2001.*

Website, www.ferrosan.com/en-US/Products/Medical-Devices/Surgiflo.aspx, description of Surgiflo Haemostatic Matrix material, one sheet printed from the Internet on May 10, 2011.

Website, www.ethicon360emea.com/products/omnex, Omnex® Surgical Sealant, two sheets printed from the internet on Jan. 10, 2012.

Website, www.ethicon360.com/products/surgiflo-hemostatic-matrix, three sheets printed from the internet on Jan. 10, 2012.

* cited by examiner

Snoring and Obstructive Sleep Apnea Treatment Plan

1002

Patient's Name: _____ Date: _____

Weight: _____ Height: _____ BMI: _____ Smoking: _____ Drinking: _____

| | Anatomical Issues | Procedures | Diagnosis/Suggested Therapy |
|---|---|---|---|
| 1008, 1018 | Deviated Septum<br>Nasal Polyps<br>Enlarged Turbinates<br>Nasal Valve Collapse | ☐ Septoplasty<br>☐ Polypectomy<br>☐ RF; Turbinectomy | 1038<br>1028 |
| Hard Palate/Soft Palate Junction 1020, 1010 | Flaccid Palatal Tissue<br>Large/Long Uvula<br>Excess Tissue | ☐ Pillar Procedure<br>☐ Uvulectomy<br>☐ UPPP | 1040<br>1030 |
| Swollen Uvula, Whitish Spots, Red Swollen Tonsils, Throat Redness, Gray Furry Tongue 1022, 1012 | Enlarged Tonsils<br>Enlarged Adenoids | ☐ Tonsillectomy<br>☐ Adenoidectomy | 1042<br>1032 |
| 1024, 1014, 1006 | Flaccid Tongue Tissue<br><br><br>Oversized Tongue<br><br><br><br>Excess/Flaccid Pharyngeal Tissue | ☐ Oral Appliance<br>☐ Repose Tongue Suspension<br>☐ GAHM*<br>☐ Oral Appliance<br>☐ Radiofrequency<br>☐ Repose Hyoid Suspension<br>☐ Repose Tongue Suspension<br>☐ GAHM*<br>☐ Repose Hyoid Suspension | 1044<br><br><br>1034<br><br>1036<br><br><br>1026 |

Category 1004
Epworth Score:
AHI/RDI:
Desat:
CPAP: ☐ Yes ☐ No
*Genioglossus and Hyoid Myotomy

1016

Category 1026
Neck Circumference:
Mueller:
Micrognathia:
Retrognathia:

MULTIPLE ORAL AND NASAL SURGICAL PROCEDURES METHOD AND KIT

CROSS REFERENCE TO RELATED PATENT APPLICATION

This application is a continuation-in-part of U.S. patent application Ser. No. 13/474,590, filed on May 17, 2012, which is a continuation-in-part of U.S. patent application Ser. No. 13/152,048, filed on Jun. 2, 2011.

BACKGROUND OF THE INVENTION

1. Field of the Invention

The present invention relates generally to the medical and surgical field, and more particularly, to a multiple oral and nasal surgical procedures and kit. The method allows the surgeon to perform the multiple oral and/or nasal surgeries during a single operative session. The kit or kits contain(s) the various instruments, medications, and other equipment required for a specific procedure or set of procedures.

2. Description of the Related Art

Ear, nose, and throat (ENT) surgery is a very important specialty in the medical field. The surgeons and medical professionals specializing in this field are highly trained and skilled in order to handle the multiple disciplines required. While an ENT surgeon may be called upon to perform only a single operation on any one of the above organs, his or her specialty is often needed to perform multiple operations on two or more of the ear, nose, and throat organs. An excellent example of a situation in which multiple ENT operations may be required is for a patient suffering from obstructive sleep apnea (OSA), where it may be necessary to perform one or more operations to improve the upper airway airflow through the mouth, throat, and nose of the patient.

In the past it was necessary for the ENT surgeon to perform a single operative procedure upon one of the subject organs (e.g., the nose) and allow time for patient healing before performing a second operation upon another organ (e.g., the mouth and/or throat). This was due to the need to place hemostatic packs of absorbent cotton or other suitable material upon the sutured or cauterized incision after the operation to stop any flow of blood that might occur. The packs would remain in place for perhaps one to two days. Obviously, a surgical procedure performed in the nose with hemostatic packs remaining in place for an extended period would require the patient to breathe through his or her mouth until the packs were removed. If an additional surgical procedure were performed on or in the mouth or throat (e.g., tonsillectomy or adenoidectomy), the irritation to the throat due to breathing through the mouth would be exceedingly uncomfortable for the patient, and might even be impossible, depending upon the throat restriction due to post-operative edema and the installed hemostatic packs.

Accordingly, it has been standard procedure to perform a single operation in one operative session, and then wait for the patient to recover before performing a subsequent operation. Clearly, this results in additional trauma to the patient and considerable additional cost, as many such procedures are sufficiently involved as to require hospitalization, at least on an outpatient basis, if not overnight. Such multiple operations also result in lower efficiencies for the hospital as well, as the hospital must arrange for and release the same patient for each surgical procedure performed. The surgeon must arrange for an operating room and staff for each surgery, as well. All in all, this has not been a cost-effective system.

Modern medicine has resulted in a number of improvements in operative and post-operative care for patients in terms of equipment, procedures, and treatments. An example of such is found in relatively recently developed hemostatic materials or treatments that may be applied to an incision to stop bleeding, rather than the older cotton or gauze packs commonly used. Examples of such treatments are the Surgicel® hemostatic sheet material and Surgiflo® hemostatic fluid (Surgicel and Surgiflo are both registered trademarks of Johnson & Johnson Corporation, of New Brunswick, N.J.), both produced by the Ethicon Company (a subsidiary of Johnson & Johnson). Other similar products are produced by other companies, as well. These treatments serve to replace the older hemostatic packs and the like, and may include analgesic and antibiotic properties as well. Many of these products are absorbed into the body after some period of time, thus precluding any requirement for removal, as would be required with stitches.

Of course, any surgical procedure requires some specific set of instruments, medications, and/or other accessories and articles. Many such surgical instruments are configured specifically to perform a specific function during a specific procedure, e.g., the insertion tool developed by the Medtronic Company used with the Pillar® palatal implant system. To this point, the surgeon has gathered the various instruments and equipment required (either reusable or disposable) for a specific procedure, prior to each operation. This clearly requires additional time in preparation, even when only a single operation or procedure is performed.

Another consideration even before the preparation for a given operation or procedure, is the determination of the specific operation or procedure to be performed. For example, in the field of obstructive sleep apnea (OSA), there may be one or more of a number of different conditions involved. These conditions may range from enlarged tonsils, adenoid and/or uvula hypertrophy, a flaccid soft palate, and/or various other conditions involving the nasal turbinate structure, lingual structure, and/or pharyngeal structure. Of course, it would be extremely rare for a single subject or patient to have all of these various conditions contributing to OSA, but it is quite common for a person to have more than one such condition. In any event, it is critical that the doctor examine the patient thoroughly in order to determine specifically what problem(s) exist(s), to determine the appropriate procedure(s) that must be performed in order to correct the problem(s).

Thus, a multiple oral and nasal surgical procedures method and kit solving the aforementioned problems is desired.

SUMMARY OF THE INVENTION

The multiple oral and nasal surgical procedures method provides a process that enables an ear, nose, and throat (ENT) surgeon to perform multiple procedures on different organs (e.g., the nose, mouth, and throat) in a single operative session. This provides great savings in time and expense for the patient, as well as saving time for the surgeon and hospital or medical facility. Most importantly, the patient undergoes a single general anesthesia rather than multiple anesthesias, thus reducing the risk of complications.

The multiple surgical procedure method is enabled by the use of hemostatic sheet material and gel, rather than conventional sutures or cauterizing of the incisions. This greatly reduces the need for conventional hemostatic packs of cotton or gauze material, which conventionally remain at the site of the incision for up to two days. Clearly, the placement of hemostatic packs in the nasal cavities for a prolonged period requires the patient to breathe orally. This generally precludes the performance of oral surgery in conjunction with nasal surgery in a single operating session. The present method of performing multiple operations in a single operating session overcomes this problem through the use of hemostatic sheet and/or gel treatments, which do not obstruct airflow through the nose. This allows the surgeon to perform multiple procedures in the nose, mouth, and/or throat in a single operating session, thus avoiding the problems of multiple patient trauma over perhaps months of operations, the need to schedule multiple hospital visits, and the need to schedule multiple operating room sessions and staff for those sessions.

The method of performing multiple surgical procedures may be applied to a number of different but related medical procedures, but is particularly well suited for the treatment of conditions causing snoring or obstructive sleep apnea (OSA). This problem can be due to a number of different conditions occurring in the nose, mouth, and throat, and it is not uncommon for a patient to require multiple operations to correct various ones of these conditions. These conditions may comprise a deviated nasal septum, tonsil and adenoid enlargement and/or hypertrophy of one or both of the inferior turbinate nasal passages, a weak or flaccid soft palate structure, and/or a flaccid tongue base. While it would be extremely rare for any one individual to have all of these conditions, it is quite common for an individual suffering from OSA to have two or more such conditions.

According to the present method, the surgeon initially evaluates the patient to determine which of several procedures are needed. An exemplary score sheet or treatment plan is provided herewith. A plurality of surgical implement or instrument kits is provided, each of the kits containing all of the articles required for a specific procedure or group of procedures. The treatment plan is used to evaluate the patient prior to scheduling the operation. A single surgery session is then scheduled and the surgeon prepares for the session in accordance with the results indicated by the score sheet or treatment plan by gathering the single kit or multiple kits of surgical instruments and equipment required for the procedure(s), as required. The surgeon performs the individual operations as indicated, using hemostatic sheet and/or gel treatments in order to preclude long-term blockage of the nasal and/or oral passages of the patient. An endotracheal tube is installed in the patient for the duration of the operations to allow the patient to breathe during the operations when the nasal cavity is packed with hemostatic material. The hemostatic packs are removed at the end of the surgery or following the completion of a given surgical procedure. This allows the patient to breathe freely even though multiple surgical procedures may have been performed in both the nasal and oral passages.

The kit or kits are preferably composed of disposable, single-use components in order to obviate the need for sterilization, repackaging, and corresponding labor costs. The provision of such disposable, single-use instruments enables the manufacturer of the instruments or other party to assemble the various instruments required for a given procedure into a kit containing those specific instruments, medications, and other equipment required for the procedure, without additional paraphernalia. The surgeon need only determine the specific procedure or procedures to be performed according to the evaluation sheet or treatment plan, and select the corresponding kit of instruments and equipment to ready himself or herself for the operation.

These and other features of the present invention will become readily apparent upon further review of the following specification and drawings.

BRIEF DESCRIPTION OF THE DRAWINGS

FIG. 10 is an evaluation chart or treatment plan for the surgeon to develop the appropriate procedure or procedures in a method of performing multiple oral and nasal surgical procedures according to the present invention.

Similar reference characters denote corresponding features consistently throughout the attached drawings.

DETAILED DESCRIPTION OF THE PREFERRED EMBODIMENTS

The method of performing multiple oral and nasal surgical procedures enables a surgeon to accomplish a series of operations in a single operating session, thereby greatly reducing trauma and cost for the patient and saving considerable time for the surgeon and patient. While the present disclosure is directed primarily to operations involving ear, nose, and throat (ENT) surgery, it will be seen that the method may be expanded to other groups of closely related surgical operations and procedures. The method employs the application of hemostatic surgical gel and/or hemostatic surgical sheet material to the surgical incisions immediately following the completion of each specific surgical procedure in lieu of suturing or cauterizing the incision, thereby greatly reducing trauma to the patient and the need to retain hemostatic packs in the nasal or oral cavities of the patient for some time after the operation(s).

Figure 1:
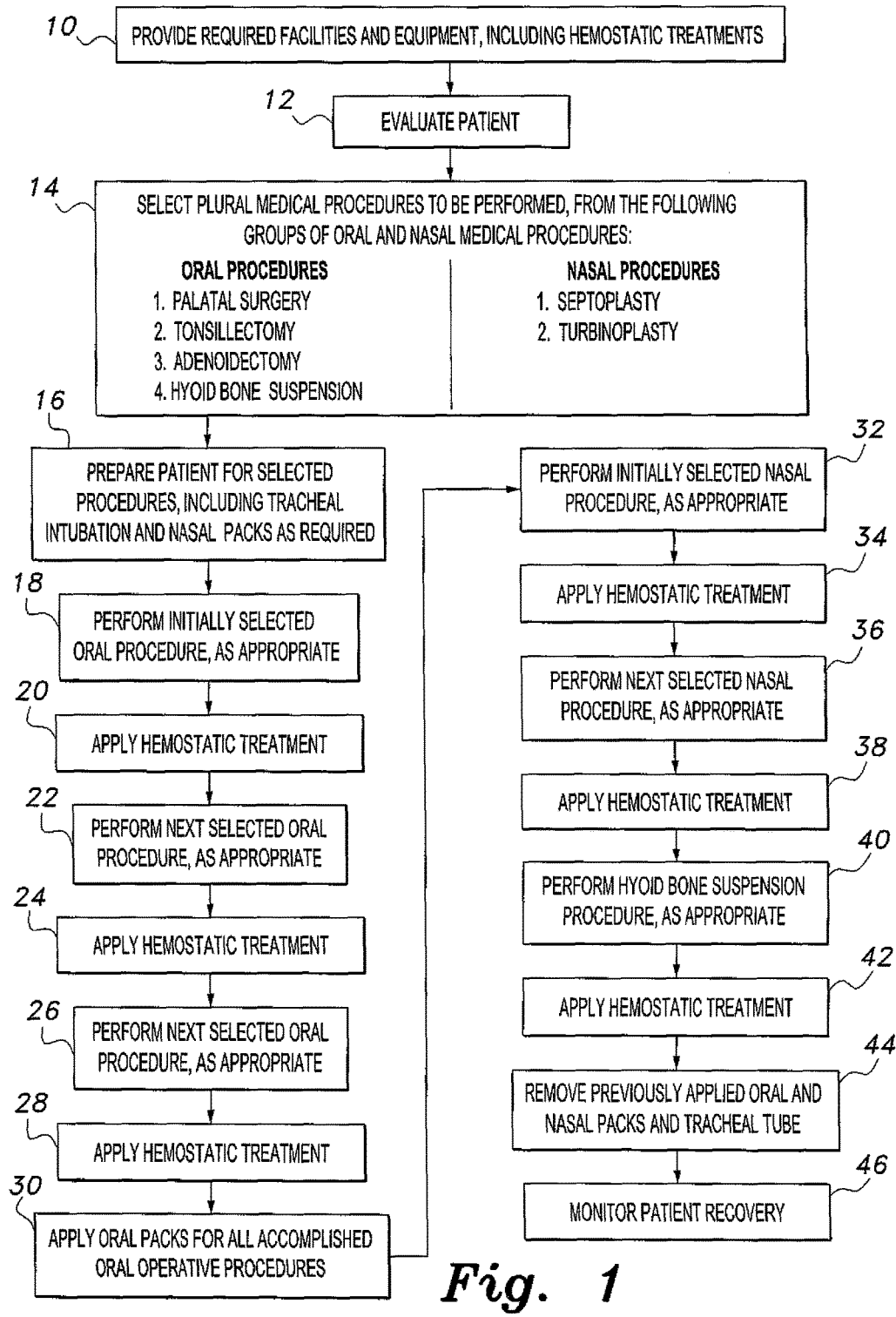
FIG. 1 is a flowchart briefly describing the basic steps in a method of performing multiple oral and nasal surgical procedures according to the present invention.

FIG. 1 provides a flowchart briefly describing the steps of the method. As in all medical procedures, the initial step is the provision of the required facilities and equipment, as generally indicated by the first step 10. The hemostatic treatments noted in the first step 10 may include an applicator preloaded with a hemostatic surgical gel and hemostatic sheet material, in addition to hemostatic packs of cotton, gauze, and/or other suitable materials. All of the above hemostatic treatments are conventional. An example of a hemostatic surgical gel and applicator is Surgiflo® hemostatic matrix, produced by the Ethicon Company. An applicator is also provided for preloading with the Surgiflo material, the applicator having a choice of cannulas or "straws" for applying the material accurately to the site of the incision. An example of a hemostatic sheet material is Surgicel®, an absorbable cellulose-based material produced by the Ethicon Company. The Surgicel® material may be cut to size for application to the incision or other surgical wound. Both the Surgiflo® and Surgicel® materials may also be treated with analgesic and/or antibiotic agents, if desired. These materials and their treatments are conventional, as noted further above.

The patient is evaluated, as generally noted in the second step 12 of the flowchart. The evaluation may comprise physical examination and/or radiological examination (e.g., x-ray), as appropriate. From this evaluation, the surgeon determines the specific surgical procedures or operations to be performed during the single operation session. The present method is applicable when the surgeon will perform at least two of the surgical procedures. These surgical procedures may comprise at least one oral and/or throat procedure and at least one nasal procedure, or may comprise plural oral procedures and no nasal procedures, or plural nasal procedures and no oral procedures. The specific surgical treatment developed is customized for the condition of each patient. While all patients may snore or may be afflicted with OSA, not all patients should receive identical treatments.

The third step 14 of the chart includes a general list of the oral and nasal procedures that may be performed by an ear, nose, and throat (ENT) surgeon, the listed procedures being exemplary of those generally performed for treating snoring and obstructive sleep apnea (OSA). It will be understood that the general method of performing two or more closely related surgical procedures and treating the incisions with non-obstructive hemostatic materials may be expanded to other areas, in addition to those listed. In the case of an ENT surgeon treating a patient suffering from OSA, the surgeon would select a plurality of procedures from the list of oral procedures comprising palatal surgery, tonsillectomy, adenoidectomy, and hyoid bone or tongue base suspension surgery (the latter procedure might more properly be considered throat or neck surgery). The palatal surgery preferably comprises the placement of Pillar® implants (Pillar is a registered trademark of Medtronic Xomed, Inc. of Jacksonville, Fla.) in the soft palate to stiffen the soft palate. However, the palatal surgery may comprise other procedures, e.g., uvulectomy or uvulopalatopharyngoplasty (UPPP) or applying radiofrequency to the area, as desired by the operating surgeon. The list of appropriate nasal procedures is somewhat larger, comprising septoplasty (for a deviated septum), turbinoplasty (to open the turbinate nasal passages), addressing the nasal valve if damaged, removal of nasal polyps or the addition of sinus surgery, or what is known as functional endoscopic sinus surgery (FESS). Again, the ENT surgeon may select a plurality of procedures solely from the oral and neck procedures or solely from the nasal procedures, or from both oral and nasal procedures, depending upon the needs of the patient.

At the time of the scheduled operations, the patient may be prepared for surgery, generally as indicated by the fourth step 16 of the flowchart. While some of the oral and nasal operations included in the present method have been conventionally performed under local anesthesia while the patient remains conscious, the patient is placed under general anesthesia and is unconscious for the multiple procedures of the present method, since at least some of the operations conventionally require general anesthesia. As both the oral and nasal breathing passages may be closed simultaneously during the surgical procedures, an endotracheal tube is placed to allow the patient to breathe during the surgical process. Other steps in the preparation process may include the placement of nasal packs having antibiotic and/or analgesic properties, as required.

At this point the patient has been prepared for surgery under general anesthesia. The surgeon begins the process by performing the first oral operation as appropriate, generally as indicated by the fifth step 18 of the flowchart. The first oral operation is selected from the group of oral operations noted in the third step 14 of the flowchart. The first oral operation may be the palatal surgery, which may comprise one of a few different surgical techniques or procedures. For example, the surgeon may elect to perform uvulectomy or uvulopalatopharyngoplasty (UPPP). However, a more recently developed process, comprising the placement of Pillar® implants in the soft palate to stiffen the soft palate, has been found to produce excellent results. This Pillar® implantation procedure has conventionally been accomplished using a local anesthetic, but the patient is placed under general anesthesia for the present multiple operation method due to the need for general anesthesia for certain other operations that may be performed under the method.

When the initial operation has been completed, a hemostatic treatment is applied to the area, generally as indicated by the sixth step 20 of the flowchart. The hemostatic treatment is in the form of a hemostatic gel, e.g., Surgiflo®, as noted further above, for hemostatic treatment of the Pillar® implantations or other palatal surgery. The hemostatic gel is applied by means of a preloaded applicator having a tube or cannula for precise placement of the gel at the desired location, as noted further above. In some instances a hemostatic sheet material, e.g., Surgicel®, may be applied in lieu of the hemostatic gel. Both the hemostatic gel and the hemostatic sheet material may include other additives to provide analgesic and/or antibiotic properties, if desired.

At this point the surgeon moves to the next planned oral operation, generally as indicated by the seventh step 22 of the flowchart. The second oral operation is selected from the remaining oral operations of the list of the second step 14 of the flowchart. Assuming the patient's tonsils are enlarged and still in place, a tonsillectomy may be indicated. Again, this would have been determined during examination of the patient well before the scheduled surgery. The surgeon performs the tonsillectomy and then applies the appropriate hemostatic treatment as noted in the eighth step 24 of the flowchart. The surgeon may elect to apply a hemostatic gel, e.g., Surgiflo® using the conventional applicator, or perhaps a hemostatic sheet material as deemed appropriate by the surgeon, without need of cautery, stitches, or conventional ties.

In the example of the present disclosure, each of the possible operations of the method is generally described, but it should be understood that it would be extremely rare for any given patient to require all of the operations. In any event, should the pre-surgical examination of the patient indicate that the adenoids should be removed, an adenoidectomy would next be performed, generally as indicated by the ninth step 26 of the flowchart, and the incisions or curetted areas treated, generally as indicated by the tenth step 28 of the flowchart. While conventional surgical techniques are used for the adenoidectomy (and other surgical procedures described herein), the method of closing the incision or curetted area relies upon the application of a hemostatic treatment in the form of a hemostatic gel or hemostatic sheet material rather than the use of cautery or packing, as conventionally performed. This results in significant reduction of trauma for the patient, allowing all of the indicated operations to be performed in a single operating session.

When each of the selected oral operations has been performed, the oral cavity is packed conventionally with hemostatic packs of cotton, gauze, and/or other suitable materials as required, generally as indicated by the eleventh step 30 of the flowchart. These oral packs remain in place only until all of the operational procedures planned for the operating session have been performed. They are removed immediately following all of the surgeries.

The above-described steps comprise all of the oral operations that may be performed in surgical treatment for obstructive sleep apnea. At this point, the surgeon shifts his or her attention to the nose of the patient and proceeds with a first nasal operation, generally as indicated by the twelfth step 32 of the flowchart. There are multiple nasal procedures that might be performed, e.g., septoplasty (to correct a deviated septum) and turbinoplasty (to shrink the inferior turbinate to enlarge the nasal passages), as indicated in the list of the third step 14 of the flowchart. Assuming that both are to be performed, the surgeon would likely elect to proceed initially to correct the deviated septum of the patient. This surgery is performed conventionally, with the surgeon applying a post-operative hemostatic treatment as described further above in lieu of conventional sutures or cauterizing of the surgical wound(s), generally as indicated by the thirteenth step 34 of the flowchart.

Assuming that the patient also required turbinoplastic surgery as well, the surgeon would then operate to correct this problem, generally as shown by the fourteenth step 36 of the flowchart. The surgical incision(s) would again be treated with an appropriate hemostatic treatment, e.g., a hemostatic gel applied by means of an appropriate conventional applicator, generally as indicated by the fifteenth step 38 of the flowchart. The nasal cavities may then be packed using conventional hemostatic cotton and/or gauze packing. The packing remains in place for the remainder of the operating session.

At this point only a single possible additional surgical procedure remains of the multiple procedures for correcting a patient's obstructive sleep apnea (OSA) condition. That single additional procedure might be grouped with the oral procedures, but is perhaps more accurately considered as part of a neck procedure. This is the relocation or anterior advancement of the hyoid bone, or the tongue base separately or in combination, generally as indicated by the sixteenth step 40 of the flowchart. This bone is located in the upper neck, and is not attached directly to any of the other skeletal structure. As it is somewhat free to move, it may cause some narrowing of the throat and subsequent restriction of airflow during sleep, i.e., sleep apnea. The hyoid bone suspension procedure involves the detachment of the upper tendons from the hyoid bone, allowing the bone to be relocated slightly forward of its original location. Hemostatic treatment is applied in the form of hemostatic sheet material (e.g., Surgicel®, or other suitable hemostatic treatment) to complete the surgery, generally as indicated by the seventeenth step 42 of the flowchart.

At this point, the previously placed oral and nasal packs remain in place, with the patient breathing by means of the endotracheal tube placed before the operations began. Accordingly, the surgeon removes the oral packing and nasal packing, checking to confirm that hemostasis has occurred, using further hemostatic gel or sheet material as appropriate. With all packing removed, the nasal and oral breathing passages of the patient are open and the previously installed endotracheal tube may be removed, generally as indicated by the eighteenth step 44 of the flowchart. The patient may then be revived to consciousness and monitored during his or her recovery, generally as indicated by the final or nineteenth step 46 of the flowchart. Thus, all of the required medical procedures indicated by preoperative examination of the patient for the treatment of his or her snoring or sleep apnea have been accomplished in a single operating session as enabled by the use of hemostatic surgical gel and sheet material in lieu of conventional suturing and/or cauterizing of the surgical incisions and wounds.

Figure 2:
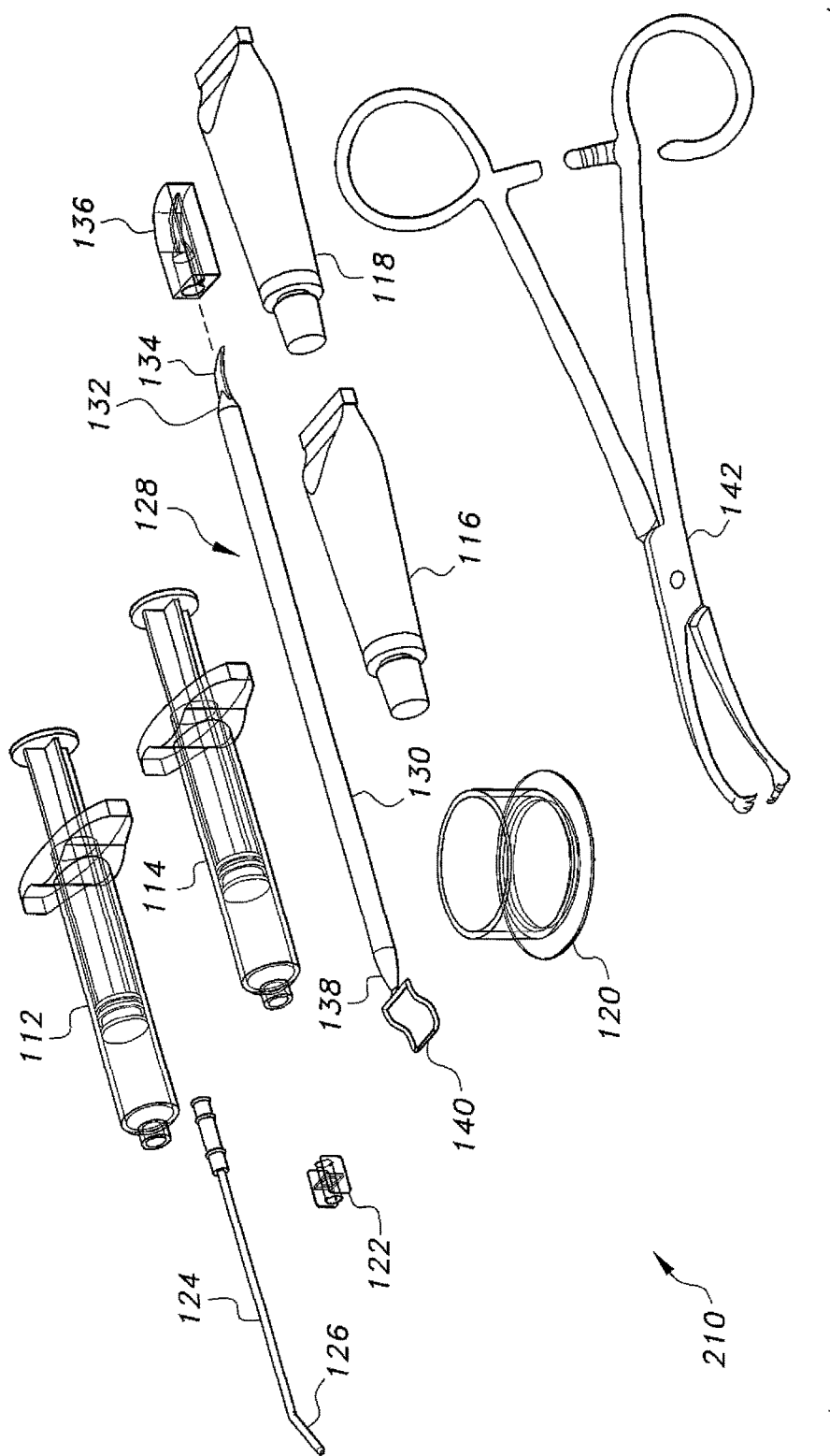
FIG. 2 is a perspective view of an exemplary embodiment of a multiple oral and nasal surgical procedures kit according to the present invention for use in performing at least one of the multiple oral and nasal surgical procedures.

FIG. 2 of the drawings is an illustration of an exemplary kit 210 of surgical implements that may be used for one or more of the procedures described further above. The kit 210 is adapted particularly for tonsillectomy or adenoidectomy surgery. The kit 210 includes first and second syringes 112, 114 for dispensing hemostatic fluid. First and second tubes (or other containers) 116 and 118 of hemostatic fluid, e.g., Surgiflo® (or other suitable agent) are provided in the kit 210 in lieu of cotton or gauze packs and the like to facilitate the multiple surgical procedures provided by the method described above. The two containers 116, 118 may contain different materials therein, e.g., saline solution, analgesics, antibacterial agents, etc. may be added to the hemostatic fluid and mixed to the desired proportion by means of the mixing container or cup 120 provided in the kit 210. An adapter 122 is also provided to connect the two syringes 112 and 114 to one another for further mixing of the contents between the two syringes 112 and 114, if required. At least one hollow cannula, e.g., the cannula 124, is provided that may be selectively installed upon either of the two syringes 112 or 114. The cannula 124 may include a curved or bent distal or tip portion 126 to facilitate the application of the hemostatic fluid. Two such cannulae may be provided with the kit 110 in order that each of the syringes 112 and 114 will have its own dedicated cannula, if desired.

A combination scalpel and curettage implement 128 is also provided with the kit 210. The combination implement 128 comprises an elongate handle 130 having a first end 132 with a scalpel blade 134 extending therefrom. The blade 134 is preferably a #12 blade, but other blade sizes may be incorporated into the implement 128. A removable cover 136 is provided for the blade 134 for safety when the scalpel is not in use. The opposite second end 138 of the combination implement 128 includes a curettage blade 140 extending therefrom. The combination implement 128 reduces the need for multiple surgical implements in the kit 210.

In addition to the above instruments and implements, the kit 210 may include a pair of surgical forceps 142. The forceps 142 may be formed of conventional surgical steel to provide for sterilization for reuse after each operating session. Alternatively, the forceps 142 may be configured for a single use and may be disposed of after the surgical procedure, but the structure of such forceps would likely result in an implement that would be more economically sterilized for reuse, rather than requiring new forceps for each kit.

Figure 3:
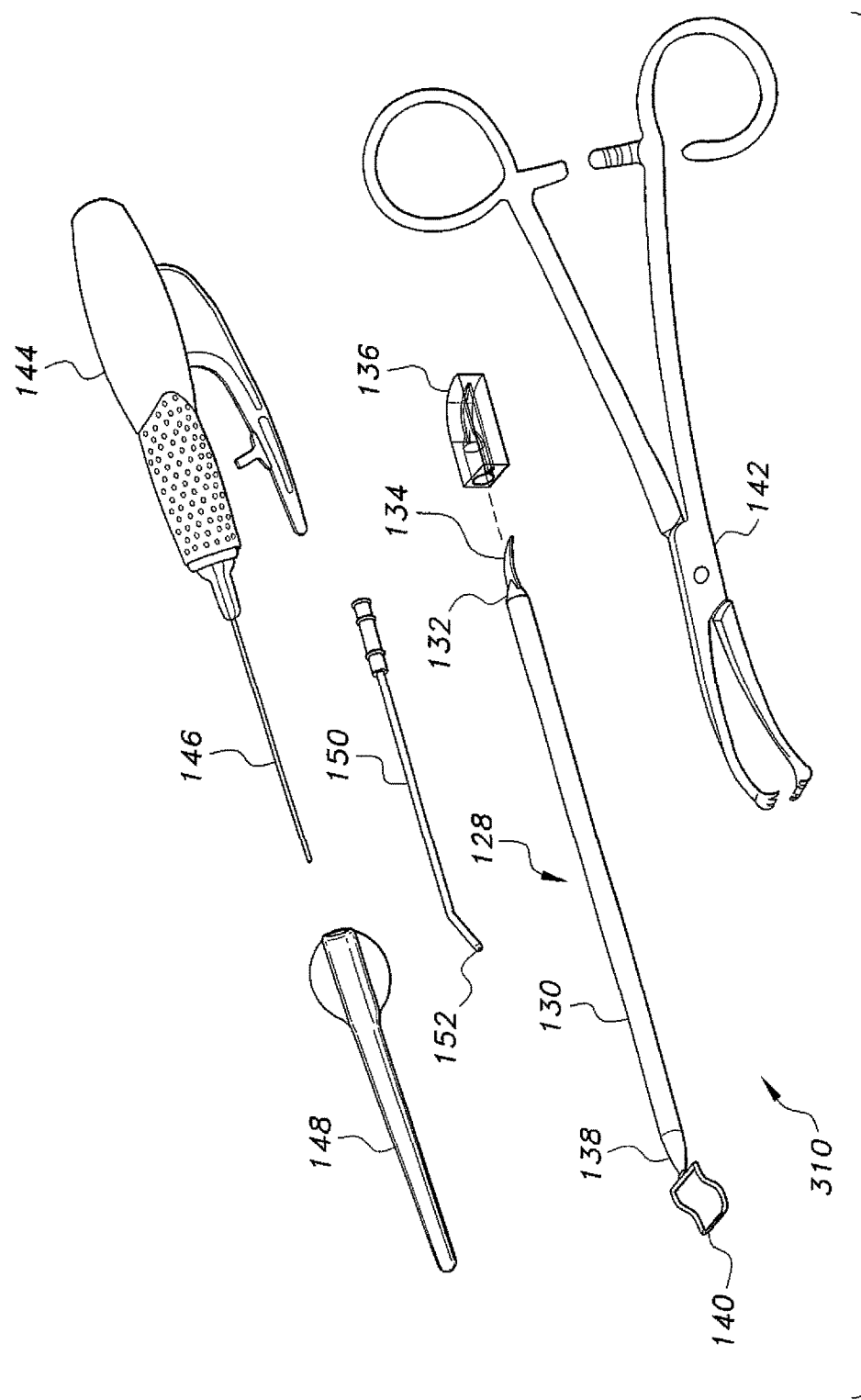
FIG. 3 is a perspective view of a second embodiment of a multiple oral and nasal surgical procedures kit according to the present invention for use in performing at least one of the multiple oral and nasal surgical procedures.

FIG. 3 of the drawings illustrates another kit 310 containing an alternative selection of instruments or implements. The kit 310 includes the combination scalpel and curettage implement 128 included in the kit 210 of FIG. 2, as well as the forceps 142. In addition to the above, the kit 310 of FIG. 3 includes an applicator 144 for the application of a surgical sealant or adhesive (e.g., Omnex®) or the like to a surgical site. The applicator includes a thin applicator cannula 146 and a cover or guard 148 therewith, but a secondary dispensing cannula 150 having a curved or bent distal end or tip portion 152 may be provided to facilitate application of the sealant to restricted surgical sites, e.g., for the attachment of a graft material, such as Durepair® (a collagen matrix manufactured by the Medtronic Company) in the repair of the tympanic membrane of the ear. The surgical sealant or adhesive may also serve a hemostatic function as well.

Figure 4:
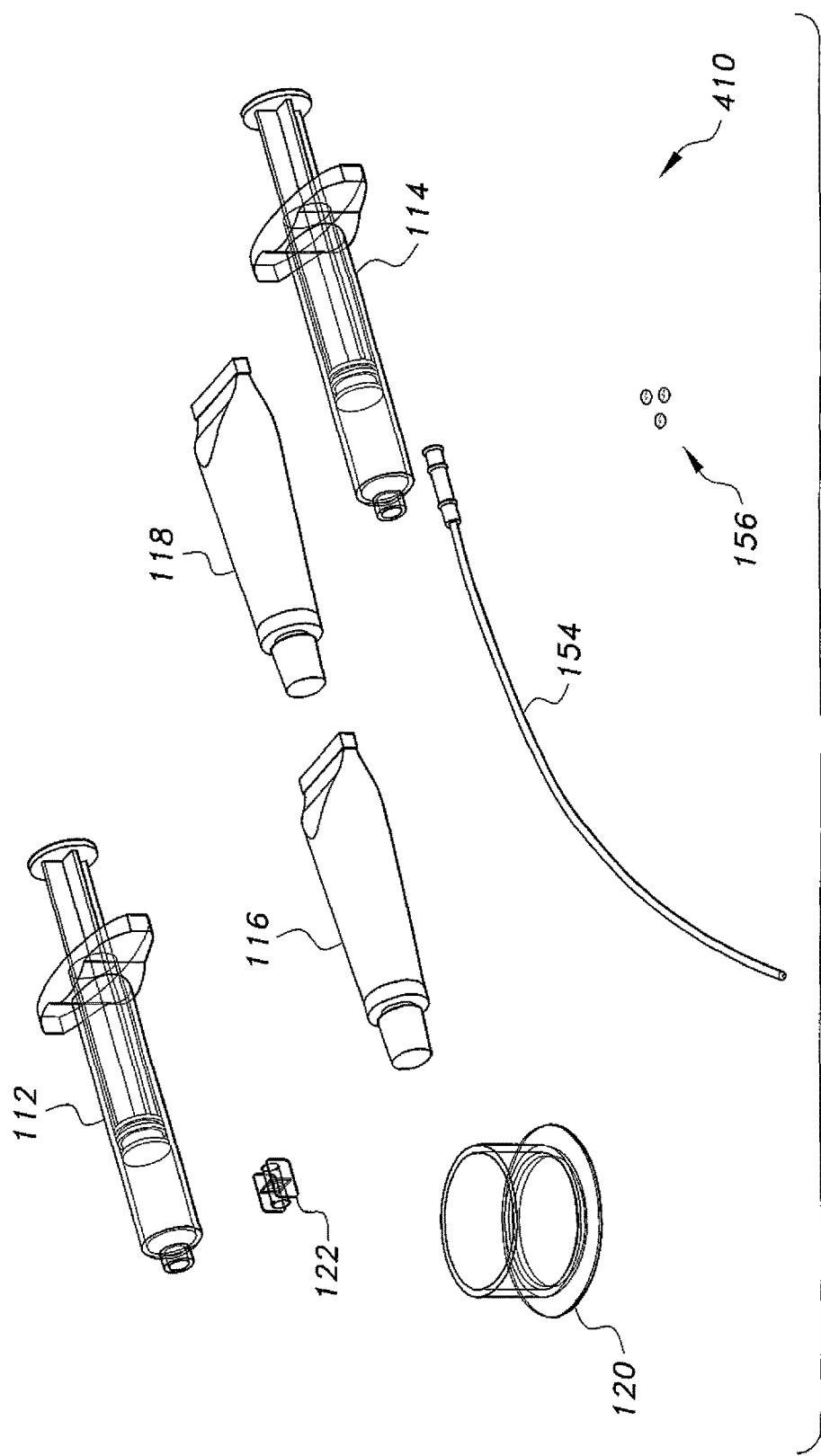
FIG. 4 is a perspective view of a third embodiment of a multiple oral and nasal surgical procedures kit according to the present invention for use in performing at least one of the multiple oral and nasal surgical procedures.

The surgical implement kit 410 of FIG. 4 includes another alternative selection of implements. The surgical implement kit 410 includes the two syringes 112 and 114, the two containers or tubes 116 and 118, the mixing cup 120, and the syringe adapter 122 of the kit 210 of FIG. 2, but also includes a flexible applicator or dispensing cannula 154. The surgical implement kit 410 may further include sufficient sealant 156 (e.g., three drops or so of Omnex® or the like, as described further above) to serve as an adhesive for graft material when such is required, depending upon the specific surgical procedure. The sealant drops 156 are shown removed from any container or packaging, but it will be understood that such sealant 156 is normally provided in a sealed container.

Figure 5:
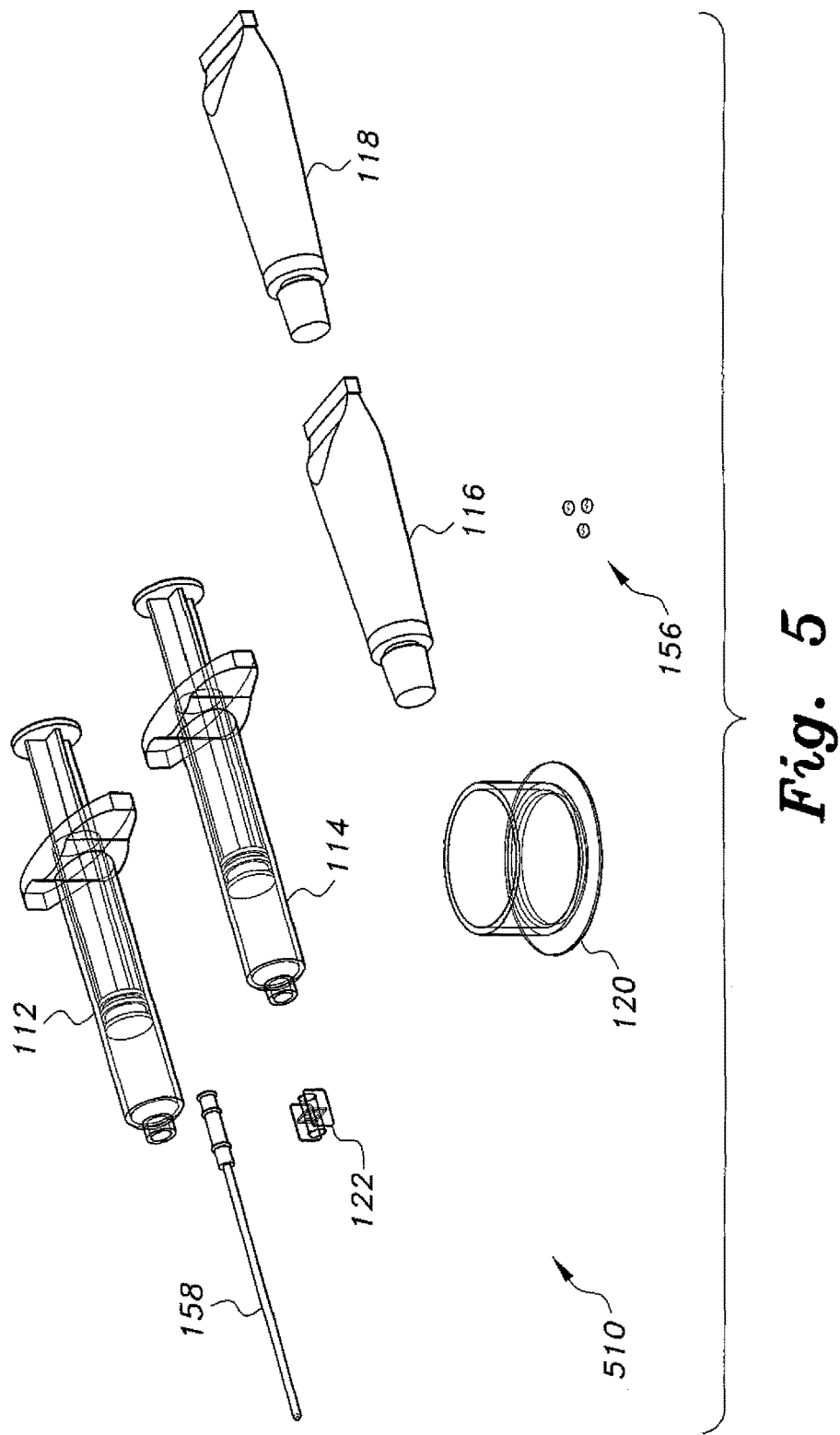
FIG. 5 is a perspective view of a fourth embodiment of a multiple oral and nasal surgical procedures kit according to the present invention for use in performing at least one of the multiple oral and nasal surgical procedures.

FIG. 5 illustrates another surgical implement kit 510. The kit 510 of FIG. 5 includes the two syringes 112 and 114, the two containers or tubes 116 and 118, the mixing cup 120, and the syringe adapter 122 of the kit 110 of FIG. 2. However, rather than having a dispensing cannula with a bent or curved distal portion, the dispensing cannula 158 of the kit 510 of FIG. 5 is straight. The cannula 158 may be formed of a thin, flexible plastic tube or other suitable material to allow it to be curved or bent to facilitate access to the desired site, but it is not pre-formed with such a bend or curve.

Figure 6:
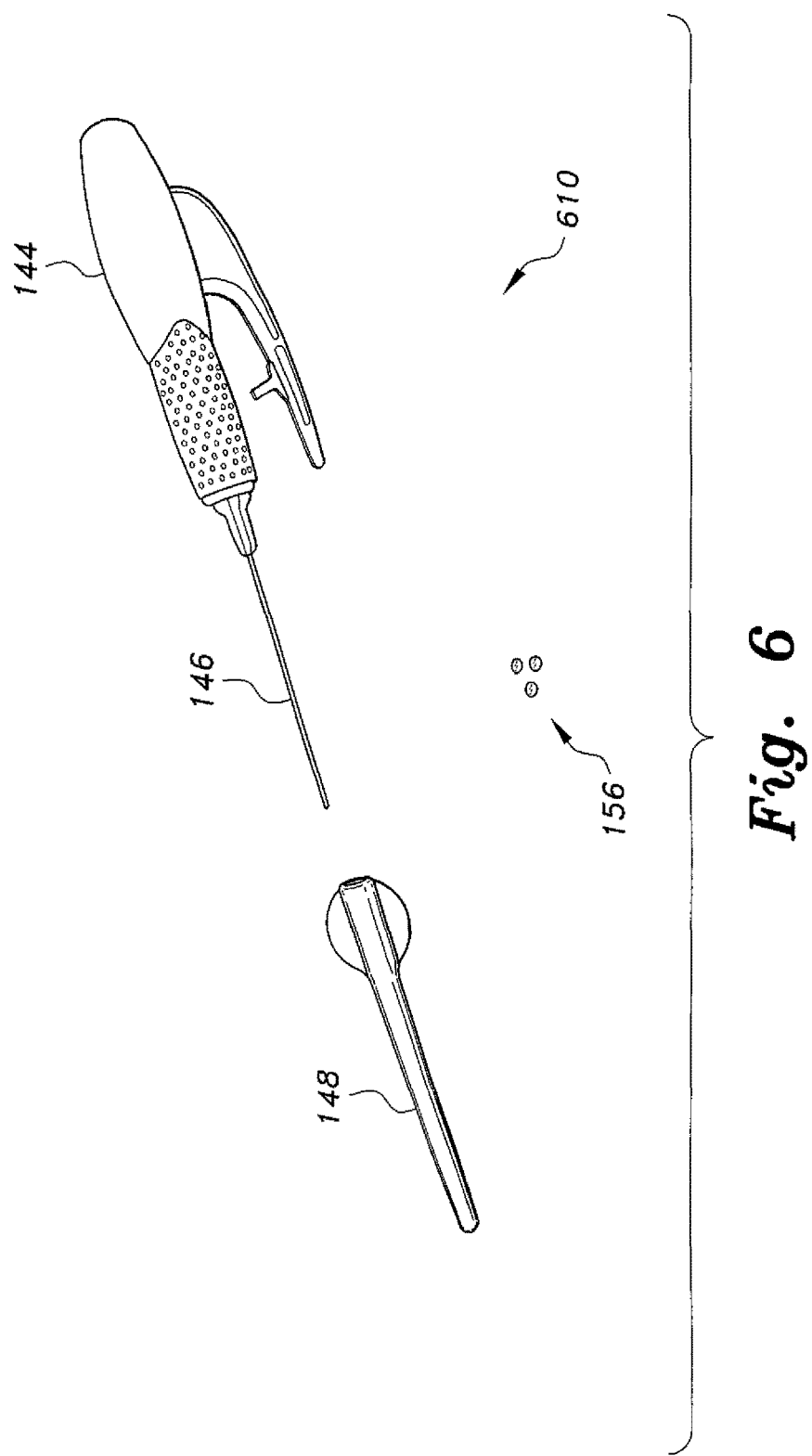
FIG. 6 is a perspective view of a surgical sealant applicator, which may be included as one of the components of at least one of the embodiment of a multiple oral and nasal surgical procedures kit according to the present invention.

The kit 610 of FIG. 6 includes only the applicator 144 and its cannula 146 and cover or guard 148 of the kit 310 of FIG. 3, along with the sealant 156 of the kits 410 and 510 respectively of FIGS. 4 and 5. As the kit 610 is intended only for the adhesive repair of an organ, e.g., an eardrum, etc., other implements of other kits (e.g., forceps 142, etc.) may be omitted from this kit 610.

Figure 7:
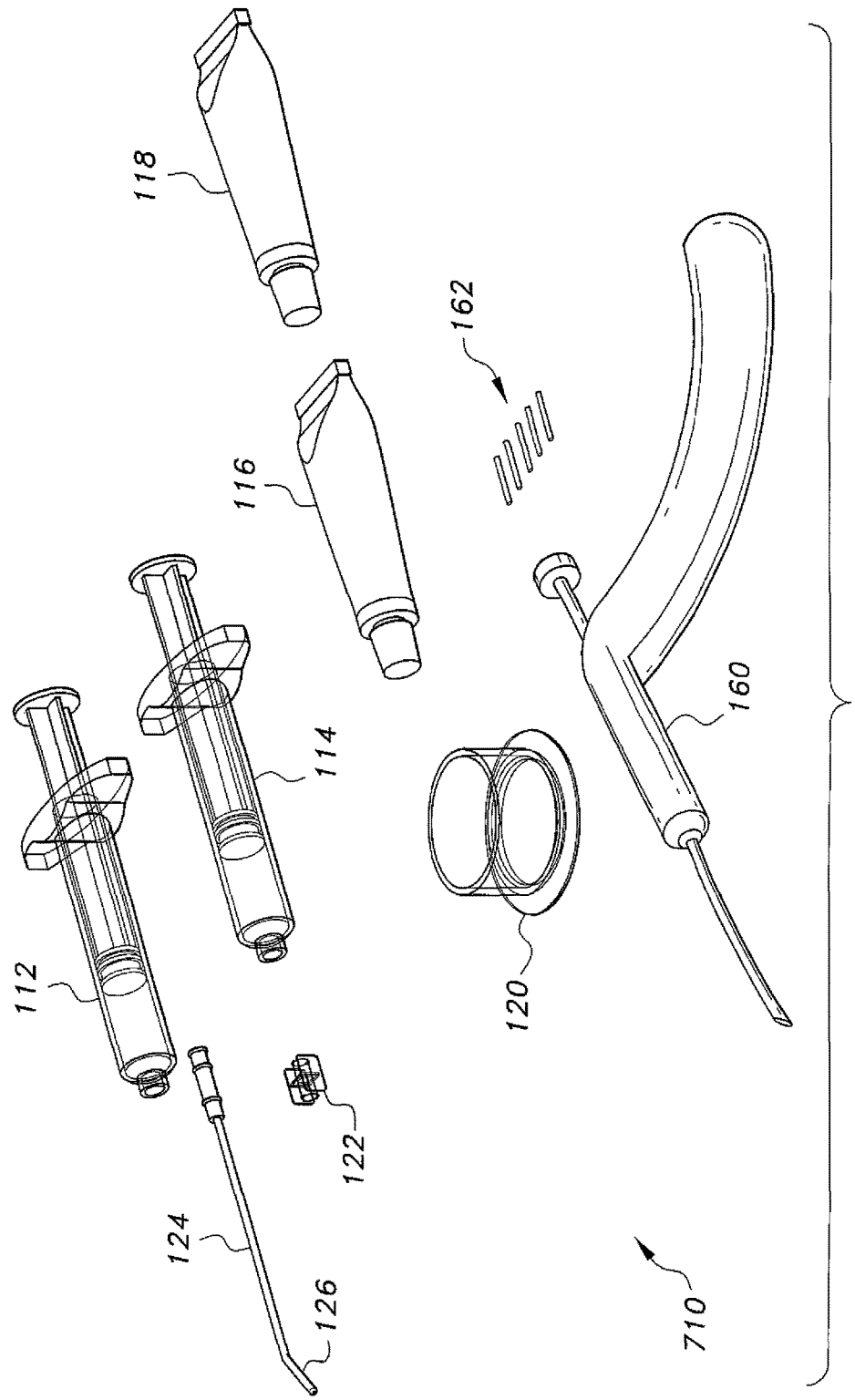
FIG. 7 is a perspective view of a fifth embodiment of a multiple oral and nasal surgical procedures kit according to the present invention for use in performing at least one of the multiple oral and nasal surgical procedures.

FIG. 7 illustrates a kit 710 that is directed specifically to the installation of implants in the soft palate for the stabilization of the soft palate as treatment for snoring and obstructive sleep apnea (OSA). The kit 710 includes the two syringes 112 and 114, the two tubes or containers 116, 118 of hemostatic gel, the mixing cup 120, the adapter 122, and the curved or bent applicator or dispensing cannula 124 of certain other kits, and also includes a soft palate implant tool 160 and a series of soft palate implants 162. The implant tool 160 and implants 162 comprise the Pillar® palatal implant system, manufactured by Medtronic Xomed, Inc.

Figure 8:
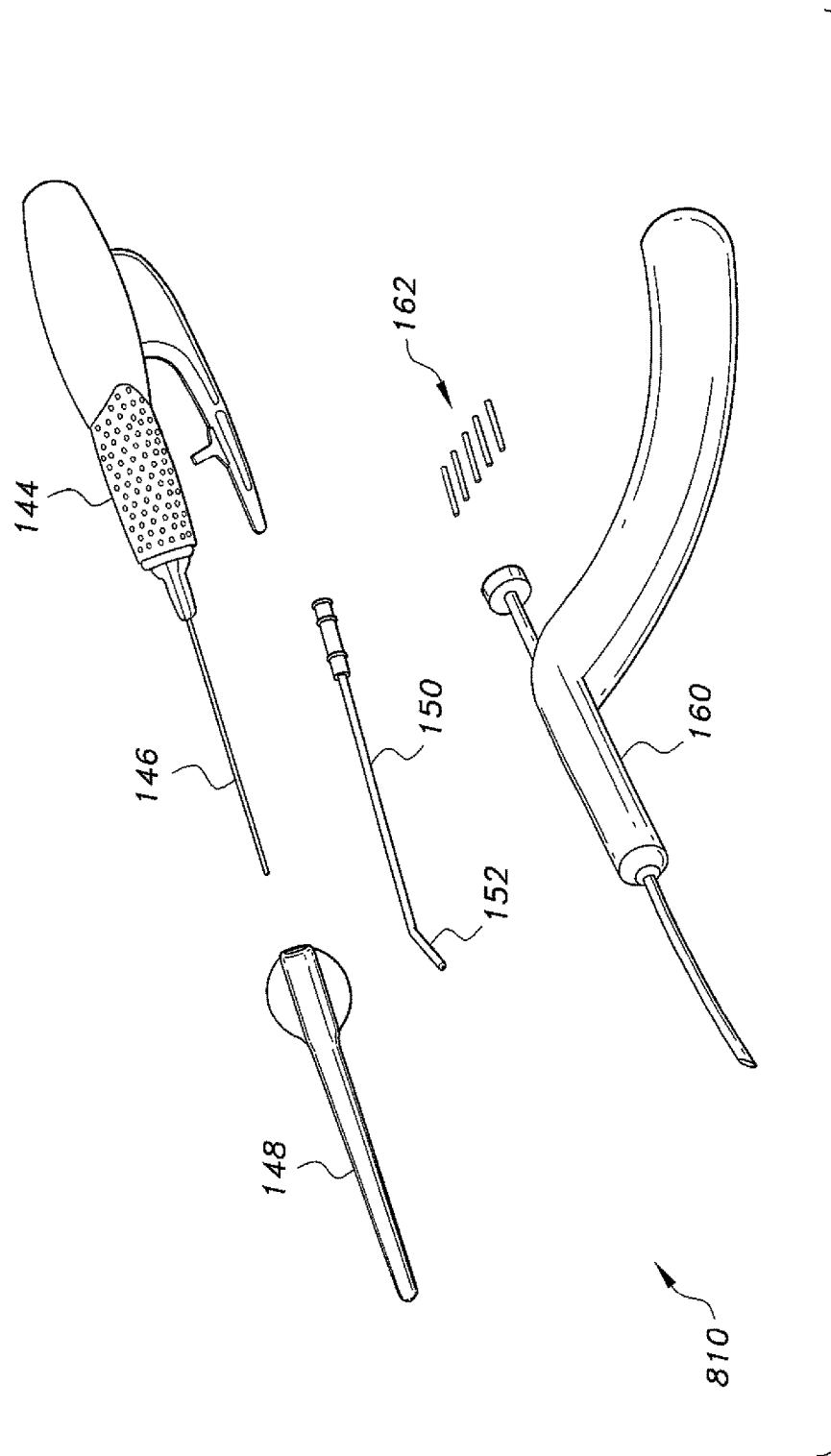
FIG. 8 is a perspective view of a sixth embodiment of a multiple oral and nasal surgical procedures kit according to the present invention for use in performing at least one of the multiple oral and nasal surgical procedures.

The kit 810 of FIG. 8 includes the applicator 144 and its cannula 146 and cover or guard 148 of the kit 310 of FIGS. 3 and 6, along with the secondary dispensing cannula 150 shown in FIG. 3. The kit 810 also includes the soft palate implant tool 160 and series of soft palate implants 162 of the kit 710 of FIG. 7. The functions of these various implements have been described further above. Preferably, the surgeon will have all of the kits of FIGS. 2 through 8 at his disposal and may quickly select the combination of kits needed for the multiple procedures contemplated for the individual patient undergoing surgery, depending upon the results according to the preoperative score sheet.

Figure 9:
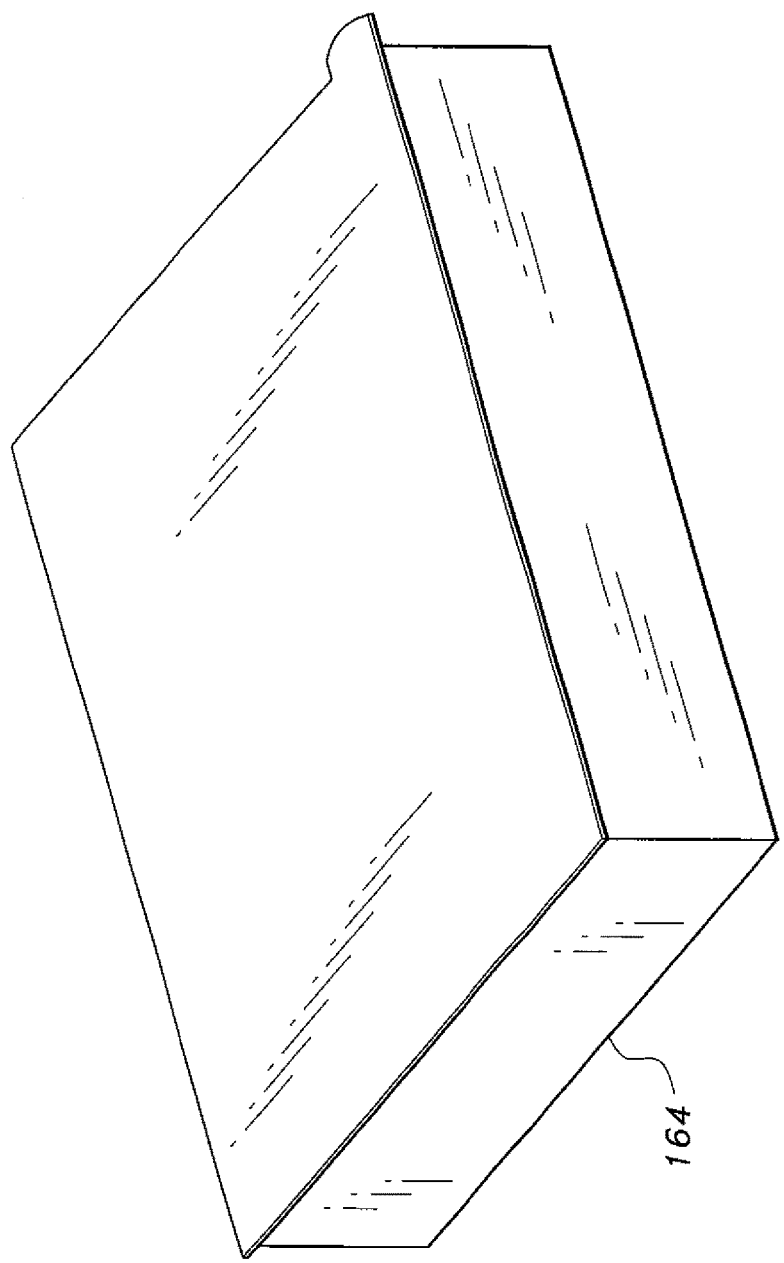
FIG. 9 is a perspective view of a disposable container adapted for holding at least one of the embodiments of a multiple oral and nasal surgical procedures kit according to the present invention.

FIG. 9 of the drawings provides an illustration of an exemplary container 164 for the containment of the various articles or implements comprising any of the various kits 210 through 810 respectively of FIGS. 2 through 8. The exemplary container 164 of FIG. 9 is configured to contain the syringes 112 and 114 and one or more dispensing cannulae 124, the tubes or containers 116 and 118 of hemostatic fluid and the mixing cup 120, the combination scalpel and curettage implement 128, and the forceps 142. All of these implements may be sealed within the internally sterilized container 164. Individual pockets or receptacles may be provided within the container 164 for the secure containment of the various implements therein. The container 164 is preferably formed of economically disposable materials to provide for convenient disposal once the container 164 has been unsealed and the various implements have been removed therefrom and used.

FIG. 10 is an illustration of a treatment plan chart 1000 for the evaluation of a patient having snoring and/or obstructive sleep apnea (OSA) problems. The chart 1000 may include a first patient data area 1002 for the entry of statistics, such as basic height, weight, body mass index, etc., and a second patient data area 1004 relating to various medical issues of the patient. The chart 1000 is further divided into a series of four columns. The first column 1006 contains a series of anatomical representations comprising a nasal anatomical representation 1008, oral and tracheal anatomical representations 1010 and 1012, and a lingual anatomical representation 1014. The second column 1016 includes a series of four sets of anatomical issues related to the anatomical representations 1008 through 1014 of the first column 1006. These sets of anatomical issues comprise a group of nasal anatomical issues 1018, oral and tracheal anatomical issues 1020 and 1022, and lingual anatomical issues 1024. The third column 1026 comprises corresponding sets of procedures to address the issues 1018 through 1024. This procedures column 1026 includes a group of nasal procedures 1028, first and second groups of oral and tracheal procedures 1030 and 1032, and a group of lingual procedures 1034. Finally, the fourth column 1036 comprises areas to note diagnoses and/or suggested therapies for the corresponding issues and procedures. The first area 1038 of the fourth column 1036 is for notes regarding diagnosis and/or therapy of the nasal anatomy. The second and third areas 1040 and 1042 serve for the diagnosis and therapy of the two oral and tracheal aspects and the fourth area 1044 serves for the diagnosis and therapy of the lingual anatomy.

This treatment plan chart 1000 provides a single form for the doctor or medical professional to consider all of the critical factors concerning the patient, as well as all of the various anatomical issues or conditions and the corresponding procedures so the doctor can arrive at a diagnosis and proposed therapy for each of the conditions. Moreover, the chart 1000 provides a means for the doctor or medical professional to evaluate the severity of the OSA disorder, using a specific predictive and elaborate quantitative system. The various conditions or issues may be categorized into five separate divisions. Various conditions or issues of each division may be assigned a numerical value. The following table itemizes this evaluation system.

TABLE 1

OSA Severity Scoring System

| DIVISION | CONDITION | SCORE |
|---|---|---|
| Sinonasal (8 possible points) | Frontal Sinus | 1 |
| | Ethmoid Sinus | 1 |
| | Maxillary Sinus | 1 |
| | Sphenoid Sinus | 1 |
| | Nasal Septum | 1 |
| | Nasal Polyps | 1 |
| | Nasal Valve | 1 |
| | Nasal Turbinates (Inferior, Middle, & Combined) | 1 |
| Tonsil (1 point) | Tonsillitis, Enlarged Tonsils, etc. | 1 |
| Adenoid/PNS Mass (1 point) | Enlarged/Infected Adenoids, etc. | 1 |
| Tongue Base (1 point) | Displaced Tongue Base, or Other Tongue Condition | 1 |
| Soft Palate (1 point) | Flaccid Soft Palate, or Other Soft Palate Condition | 1 |

In accordance with Table 1, a total of twelve points is possible, given the above conditions, but the table above may be modified and revised to include other conditions, if desired. The doctor or medical professional can consider each condition that the patient may have and arrive at a numerical total that relates to the severity of the OSA condition of the patient. The doctor may then determine an appropriate, comprehensive, single-stage, multi-level course of action in accordance with the multiple surgical methods described further above, and select the corresponding kit or kits of surgical implements required to carry out the surgical procedures successfully.

Figure 11:
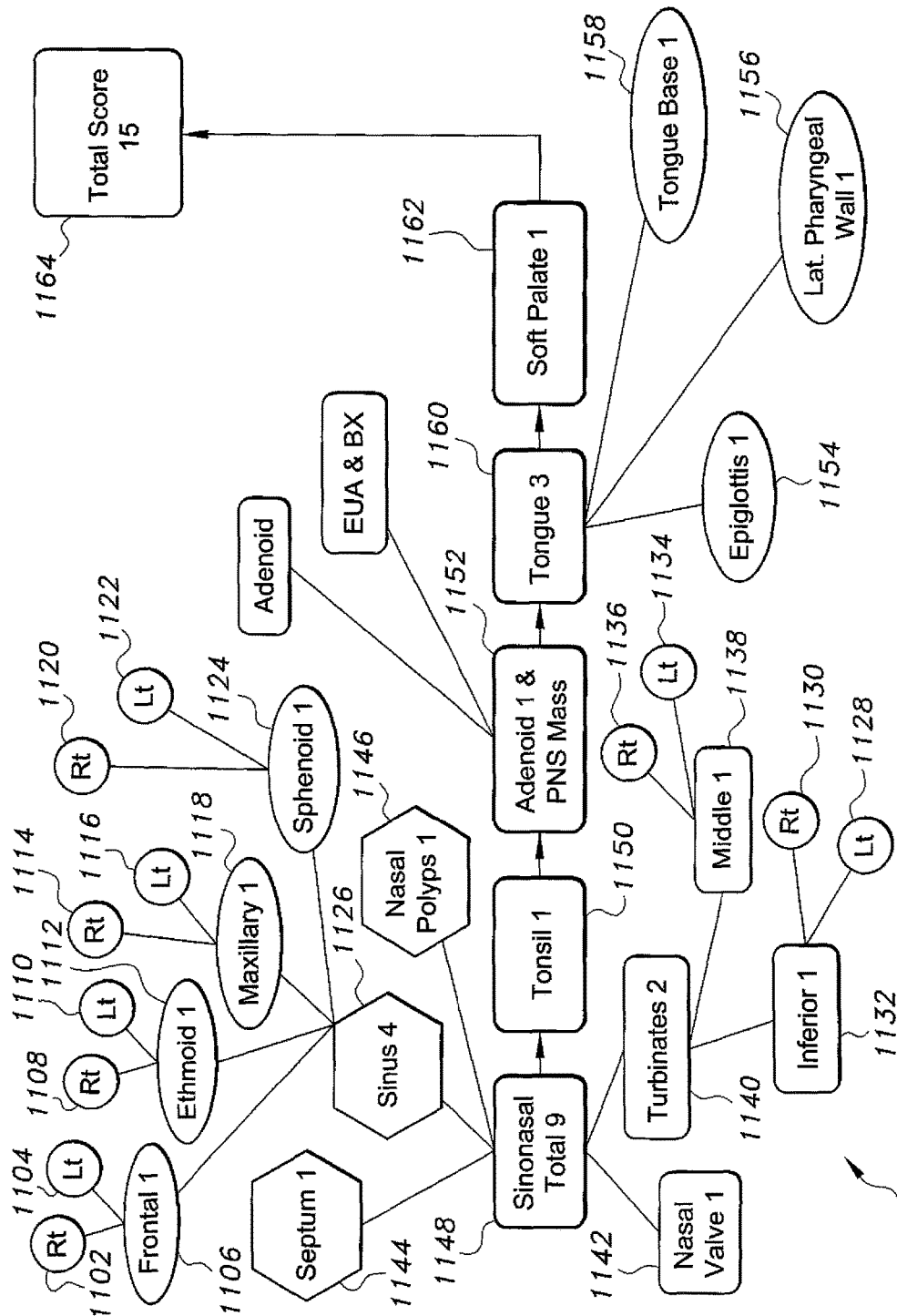
FIG. 11 is a flowchart illustrating the various potential oral and nasal conditions and corresponding values to enable the surgeon to evaluate the overall condition of the patient pursuant to the method of performing multiple oral and nasal surgical procedures according to the present invention.

FIG. 11 provides an alternative chart showing a somewhat more detailed protocol for the evaluation of a patient suffering from obstructive sleep apnea. The protocol 1100 of FIG. 11 includes all of the various organs listed in Table 1 above, but refines the divisions by breaking down the nasal turbinates into inferior and middle turbinates and breaking down the tongue into the tongue base, epiglottis, and lateral pharyngeal wall. This expands the total possible point count from twelve, in Table 1, to fifteen.

The protocol 1100 of FIG. 11 includes left and right frontal sinus units 1102 and 1104, which are linked to a total frontal sinus unit 1106. The protocol further includes left and right ethmoid sinus units 1108 and 1110 linked to a total ethmoid sinus unit 1112, left and right maxillary sinus units 1114 and 1116 linked to a total maxillary sinus unit 1118, and left and right sphenoid sinus units 1120 and 1122 linked to a total sphenoid sinus unit 1124. Each of the total sinus units, i.e., the frontal 1106, ethmoid 1112, maxillary 1118, and sphenoid 1124, may be assigned a score of either zero or one, depending upon the findings of the examination. An exemplary score of one is indicated in each of these units 1106, 1112, 1118, and 1124 in FIG. 11. Each of these units 1106, 1112, 1118, and 1124 is linked to a cumulative sinus unit 1126, with this unit showing an exemplary score or point total of four due to the single point assigned to each of the four sinus areas as discussed above.

The nasal turbinates are categorized as left and right inferior turbinate units 1128 and 1130 linked to a total inferior turbinate unit 1132 and left and right middle or medial turbinate units 1134 and 1136 linked to a total middle turbinate unit 1138. The total inferior turbinate unit 1132 and total middle turbinate unit 1138 are each assigned a score or value of either zero or one, depending upon the findings during the examination. The total inferior turbinate unit 1132 and total middle turbinate unit 1138 are in turn linked to a cumulative turbinate unit 1140, with the maximum potential totals from the two total units (one point each) being shown in the cumulative turbinate unit 1140. The sinonasal area further includes a nasal valve unit 1142, a nasal septum unit 1144, and a nasal polyp unit 1146, with each of these units also being assigned a point score or value of either zero or one, depending upon the results of the examination.

The cumulative sinus unit 1126, cumulative turbinate unit 1140, nasal valve unit 1142, nasal septum unit 1144, and nasal polyp unit 1146 are each linked to a sinonasal total unit 1148. The sinonasal total unit 1148 may have a maximum point value or score of nine, as a result of the additive scores of the cumulative sinus unit 1126 (e.g., four), the cumulative turbinate unit 1140 (e.g., two), the nasal valve unit 1142 (one), the nasal septum unit 1144 (one), and the nasal polyp unit 1144 (one). As noted further above, it would be extremely rare for any given patient to have sinonasal conditions that would result in a maximum point score of nine for these organs. The points or values illustrated in the protocol form of FIG. 11 are maximum values to be assigned to the respective organs in the event of the examination finding conditions that require correction.

The sinonasal total unit is linked to the tonsil unit 1150. The tonsils are essentially a separate organ, and have no ancillary organs or units linked thereto. The tonsil unit 1150 is assigned a point value or score of either zero or one, depending upon the findings of the examination.

An adenoid and PNS (post nasal space) mass unit 1152 is linked to the tonsil unit 1150. At least a portion of the adenoid examination is carried out under anesthesia, as indicated by the EUA (examination under anesthesia) link to the adenoid and PNS unit 1152. The adenoid and PNS mass unit 1152 may have a point value of either zero or one, as in other units described further above.

Examination of the tongue area considers three different factors: The epiglottis, the lateral pharyngeal wall, and the tongue base. These three factors are indicated in FIG. 11 as the epiglottis unit 1154, lateral pharyngeal wall unit 1156, and tongue base unit 1158. Each of these units is assigned a value of either zero or one, depending upon the results of the examination. Each of these units 1154 through 1158 is linked to the tongue unit 1160, with the maximum point total (three) of the units 1154 through 1158 being indicated in the tongue unit 1160.

Finally, a soft palate unit 1162 is linked to the tongue unit 1160. The soft palate is an individual organ with no subdivisions, and is thus assigned a maximum score of one.

The protocol 1100 of FIG. 11 thus provides for a maximum score or point value of fifteen. The four sinus units 1106, 1112, 1118, and 1124 provide a maximum potential score of four, as indicated in the cumulative sinus unit 1126. The inferior and middle turbinates have a potential total score of two, as indicated in the cumulative turbinate unit 1140. The nasal valve unit 1142, septum unit 1144, and nasal polyp unit 1146 are each worth a potential of one point, with the four sinus points, the two turbinate points, and the three nasal points resulting in a potential total of nine points for this area. The tonsil unit 1150 and adenoid unit 1152 are worth one additional point each, for an additive total of eleven points to this stage of the protocol. The epiglottis 1154, lateral pharyngeal wall, 1156, and tongue base 1158 are each worth one point, with the cumulative tongue unit 1160 carrying a potential score of three points as a result. The three potential points of the cumulative tongue unit 1160 combined with the eleven points of the previously described units results in a maximum potential score of fourteen points through this stage. Finally, the single potential point of the soft palate unit 1162 results in a total maximum potential point value or score of fifteen points, as indicated in the total score area 1164.

A mnemonic has been developed to describe the five primary or cumulative areas or units of the protocol 1100 of FIG. 11. The cumulative sinonasal unit 1148 is designated by the letter S. The tonsil unit 1150 is designated by the letter T. The adenoid and PNS mass unit is designated by the letter A. The cumulative tongue unit 1160 is designated by a second T, while the soft palate unit 1162 is designated by a second S. Arranging these letters in the order of their units in the protocol of FIG. 11 results in the mnemonic STATS.

Each of the letters of the mnemonic STATS is assigned a numerical value in accordance with the point value or score determined during the examination of the patient. As an example, if the examining physician determined that there were two sinonasal conditions that required treatment or correction, he or she would indicate this as S2. If there were no problems with the tonsils, the physician would indicate this as T0. In the event that there was some problem with the adenoids (e.g., hypertrophy, etc.), the physician would indicate such using the designation A1. A single problem with the epiglottis, lateral pharyngeal wall, or tongue base would result in a score of one for the cumulative tongue unit, and would be designated as T1. Finally, if examination of the soft palate did not show any problems, the soft palate would receive a designation of S0. The result could be assembled as S2T0A1T1S0, forming a concise and easily remembered and interpreted description of the oral and nasal condition of a person suffering from obstructive sleep apnea. Such a shorthand system may serve as a universal code for all ear, nose, throat (ENT) physicians and surgeons, thus greatly simplifying and improving communications between such physicians when discussing the condition of a given patient.

Examination of the patient proceeds along the lines described further above in the discussion of the chart 1000 of FIG. 10. A more detailed discussion of that examination is presented here. Initially, the patient is presented with a medical history questionnaire with questions such as age, height, weight, personal habits such as smoking and/or drinking, etc. Additional tests are performed, with the additional tests comprising a nasal endoscopy, computerized tomography (CT) scan of the sinuses, performing a sleep study and sleep endoscopy, and a physical examination of the sinonasal, tonsil, adenoid, tongue, and soft palate organs of the patient. It is important that all of these tests be performed, to assure that none of the potential problem areas are overlooked. The results of the examination of each area, organ, or organ group are recorded quantitatively, i.e., as either a zero (indicating normal structure and function, no correction is needed) or one (indicating that some form of correction is needed). The results are recorded in the STATS format described further above. The results of the questionnaire are evaluated by the physician, along with the quantitative results of the above tests. The physician then decides upon the appropriate sleep apnea treatment for the patient from the quantitative values determined during the examination and recorded in accordance with the STATS format described further above. Appropriate surgery is scheduled and the appropriate kit or kits selected in accordance with the procedure described further above, depending upon the specific surgical procedure or multiple procedures to be carried out in accordance with the STATS evaluation.

The methods outlined above can be assembled and summarized as follows:

A method of evaluating the oral and nasal organs of a person having obstructive sleep apnea, comprising the steps of:

(a) performing a nasal endoscopy of the person;

(b) performing a computerized tomography scan of the sinuses of the person;

(c) performing a sleep study of the person;

(d) performing a sleep endoscopy of the person;

(e) performing a quantitative evaluation of the left and right frontal sinuses in accordance with the findings of steps (a) through (d);

(f) recording the results of the frontal sinus evaluation;

(g) performing a quantitative evaluation of the left and right ethmoid sinuses in accordance with the findings of steps (a) through (d);

(g) recording the results of the ethmoid sinus evaluation;

(i) performing a quantitative evaluation of the left and right maxillary sinuses in accordance with the findings of steps (a) through (d);

(j) recording the results of the maxillary sinus evaluation;

(k) performing a quantitative evaluation of the left and right sphenoid sinuses in accordance with the findings of steps (a) through (d);

(l) recording the results of the sphenoid sinus evaluation;

(m) performing a quantitative evaluation of the nasal septum in accordance with the findings of steps (a) through (d);

(n) recording the results of the nasal septum evaluation;

(o) performing a quantitative evaluation for nasal polyps in accordance with the findings of steps (a) through (d);

(p) recording the results of the nasal polyp evaluation;

(q) performing a quantitative evaluation of the nasal valve in accordance with the findings of steps (a) through (d);

(r) recording the results of the nasal valve evaluation;

(s) performing a quantitative evaluation of the left and right inferior nasal turbinates in accordance with the findings of steps (a) through (d);

(t) recording the results of the inferior nasal turbinate evaluation;

(u) performing a quantitative evaluation of the left and right middle nasal turbinates in accordance with the findings of steps (a) through (d);

(v) recording the results of the middle nasal turbinate evaluation;

(w) adding the quantitative values for the sinonasal evaluations of steps (e) through (v);

(x) performing a visual examination of the tonsils;

(y) performing a quantitative evaluation of the tonsils in accordance with the findings of the visual examination of step (x);

(z) recording the results of the tonsil evaluation;

(aa) adding the quantitative values of steps (w) and (z);

(bb) performing a nasal endoscopy of the adenoids;

(cc) performing a quantitative evaluation of the adenoids in accordance with the findings of the nasal endoscopy of step (bb);

(dd) recording the results of the adenoid evaluation;

(ee) adding the quantitative values of steps (aa) and (dd);

(ff) performing a visual examination of the tongue base, epiglottis, and lateral pharyngeal walls;

(gg) performing a quantitative evaluation of the tongue base in accordance with the findings of the visual examination of step (dd);
(hh) recording the results of the tongue base evaluation;
(ii) performing a quantitative evaluation of the epiglottis in accordance with the findings of the visual examination of step (ff);
(jj) recording the results of the epiglottis evaluation;
(kk) performing a quantitative evaluation of the lateral pharyngeal walls in accordance with the findings of the visual examination of step (ff);
(ll) recording the results of the lateral pharyngeal wall evaluation;
(mm) adding the quantitative values of steps (hh), (jj), and (ll);
(nn) adding the quantitative values of steps (ee) and (mm);
(oo) performing a visual examination of the soft palate;
(pp) performing a quantitative evaluation of the soft palate in accordance with the findings of the examinations of steps (c), (d), and (oo);
(qq) recording the results of the soft palate evaluation;
(rr) adding the quantitative values of steps (nn) and (qq), thereby arriving at a total score; and
(ss) determining the appropriate obstructive sleep apnea treatment for the person, from the quantitative values determined.

The method of evaluating the oral and nasal organs of a person having obstructive further comprises the steps of:
(a) assigning a first letter S to represent the sinonasal area of a person having obstructive sleep apnea;
(b) assigning a first letter T to represent the tonsils of the person;
(c) assigning the letter A to represent the adenoids of the person;
(d) assigning a second letter T to represent the tongue of the person;
(e) assigning a second letter S to represent the soft palate of the person;
(f) arranging the letters of the steps (a) through (e) in order to arrive at the term STATS;
(g) evaluating the sinonasal area of the person;
(h) assigning a quantitative value to the sinonasal area of the person, in accordance with the results of the evaluation of step (f);
(i) placing the quantitative value of the sinonasal area immediately following the first letter S in the series;
(j) evaluating the tonsils of the person;
(k) assigning a quantitative value to the tonsil area of the person, in accordance with the results of the evaluation of step (i);
(l) placing the quantitative value of the tonsil area immediately following the first letter T in the series;
(m) evaluating the adenoids of the person;
(n) assigning a quantitative value to the adenoid area of the person, in accordance with the results of the evaluation of step (l);
(o) placing the quantitative value of the adenoid area immediately following the letter A in the series;
(p) evaluating the tongue area of the person;
(q) assigning a quantitative value to the tongue area of the person, in accordance with the results of the evaluation of step (o);
(r) placing the quantitative value of the tonsil area immediately following the second letter T in the series;
(s) evaluating the soft palate of the person;
(t) assigning a quantitative value to the soft palate area of the person, in accordance with the results of the evaluation of step (r); and
(u) placing the quantitative value of the soft palate area immediately following the second letter S in the series, thereby completing an alphanumeric series defining the severity of the obstructive sleep apnea condition of the person.

It is to be understood that the present invention is not limited to the embodiments described above, but encompasses any and all embodiments within the scope of the following claims.

I claim:
1. A method of evaluating the oral and nasal organs of a person having obstructive sleep apnea, comprising the steps of:
(a) performing a nasal endoscopy of the person;
(b) performing a computerized tomography scan of the sinuses of the person;
(c) performing a sleep study of the person;
(d) performing a sleep endoscopy of the person;
(e) performing a quantitative evaluation of the left and right frontal sinuses in accordance with the findings of steps (a) through (d);
(f) recording the results of the frontal sinus evaluation as a value;
(g) performing a quantitative evaluation of the left and right ethmoid sinuses in accordance with the findings of steps (a) through (d);
(g) recording the results of the ethmoid sinus evaluation as a value;
(i) performing a quantitative evaluation of the left and right maxillary sinuses in accordance with the findings of steps (a) through (d);
(j) recording the results of the maxillary sinus evaluation as a value;
(k) performing a quantitative evaluation of the left and right sphenoid sinuses in accordance with the findings of steps (a) through (d);
(l) recording the results of the sphenoid sinus evaluation as a value;
(m) performing a quantitative evaluation of the nasal septum in accordance with the findings of steps (a) through (d);
(n) recording the results of the nasal septum evaluation as a value;
(o) performing a quantitative evaluation for nasal polyps in accordance with the findings of steps (a) through (d);
(p) recording the results of the nasal polyp evaluation as a value;
(q) performing a quantitative evaluation of the nasal valve in accordance with the findings of steps (a) through (d);
(r) recording the results of the nasal valve evaluation as a value;
(s) performing a quantitative evaluation of the left and right inferior nasal turbinates in accordance with the findings of steps (a) through (d);
(t) recording the results of the inferior nasal turbinate evaluation as a value;
(u) performing a quantitative evaluation of the left and right middle nasal turbinates in accordance with the findings of steps (a) through (d);
(v) recording the results of the middle nasal turbinate evaluation as a value;
(w) adding the quantitative values for the sinonasal evaluations of steps (e) through (v);
(x) performing a visual examination of the tonsils;

(y) performing a quantitative evaluation of the tonsils in accordance with the findings of the visual examination of step (x);
(z) recording the results of the tonsil evaluation as a value;
(aa) adding the quantitative values of steps (w) and (z);
(bb) performing a nasal endoscopy of the adenoids;
(cc) performing a quantitative evaluation of the adenoids in accordance with the findings of the nasal endoscopy of step (bb);
(dd) recording the results of the adenoid evaluation as a value;
(ee) adding the quantitative values of steps (aa) and (dd);
(ff) performing a visual examination of the tongue base, epiglottis, and lateral pharyngeal walls;
(gg) performing a quantitative evaluation of the tongue base in accordance with the findings of the visual examination of step (dd);
(hh) recording the results of the tongue base evaluation as a value;
(ii) performing a quantitative evaluation of the epiglottis in accordance with the findings of the visual examination of step (ff);
(jj) recording the results of the epiglottis evaluation as a value;
(kk) performing a quantitative evaluation of the lateral pharyngeal walls in accordance with the findings of the visual examination of step (ff);
(ll) recording the results of the lateral pharyngeal wall evaluation as a value;
(mm) adding the quantitative values of steps (hh), (jj), and (ll);
(nn) adding the quantitative values of steps (ee) and (mm);
(oo) performing a visual examination of the soft palate;
(pp) performing a quantitative evaluation of the soft palate in accordance with the findings of the examinations of steps (c), (d), and (oo);
(qq) recording the results of the soft palate evaluation as a value;
(rr) adding the quantitative values of steps (nn) and (qq), thereby arriving at a total score; and
(ss) determining the appropriate obstructive sleep apnea treatment for the person, from the quantitative values determined.

2. The method of evaluating the oral and nasal organs of a person having obstructive sleep apnea according to claim 1, further comprising the steps of:
(a) assigning a first letter S to represent the sinonasal area of a person having obstructive sleep apnea;
(b) assigning a first letter T to represent the tonsils of the person;
(c) assigning the letter A to represent the adenoids of the person;
(d) assigning a second letter T to represent the tongue of the person;
(e) assigning a second letter S to represent the soft palate of the person;
(f) arranging the letters of the steps (a) through (e) in order to arrive at the term STATS;
(g) evaluating the sinonasal area of the person;
(h) assigning a quantitative value to the sinonasal area of the person, in accordance with the results of the evaluation of step (f);
(i) placing the quantitative value of the sinonasal area immediately following the first letter S in the series;
(j) evaluating the tonsils of the person;
(k) assigning a quantitative value to the tonsil area of the person, in accordance with the results of the evaluation of step (i);
(l) placing the quantitative value of the tonsil area immediately following the first letter T in the series;
(m) evaluating the adenoids of the person;
(n) assigning a quantitative value to the adenoid area of the person, in accordance with the results of the evaluation of step (l);
(o) placing the quantitative value of the adenoid area immediately following the letter A in the series;
(p) evaluating the tongue area of the person;
(q) assigning a quantitative value to the tongue area of the person, in accordance with the results of the evaluation of step (o);
(r) placing the quantitative value of the tonsil area immediately following the second letter T in the series;
(s) evaluating the soft palate of the person;
(t) assigning a quantitative value to the soft palate area of the person, in accordance with the results of the evaluation of step (r); and
(u) placing the quantitative value of the soft palate area immediately following the second letter S in the series, thereby completing an alphanumeric series defining the severity of the obstructive sleep apnea condition of the person.

3. The method of evaluating the oral and nasal organs of a person having obstructive sleep apnea according to claim 1, further comprising:
wherein the recordation of the results of the evaluations in each of the steps (f), (g), (j), (l), (n), (p), (rr), (t), (v), (v), (z), (dd), (hh), (jj), (ll), and (qq) further includes a quantitative evaluation of:
a left frontal sinus unit;
a right frontal sinus unit;
a total frontal sinus unit, the left frontal sinus unit and the right frontal sinus unit being linked to the total frontal sinus unit;
a left ethmoid sinus unit;
a right ethmoid sinus unit;
a total ethmoid sinus unit, the left ethmoid sinus unit and the right ethmoid sinus unit being linked to the total ethmoid sinus unit;
a left maxillary sinus unit;
a right maxillary sinus unit;
a total maxillary sinus unit, the left maxillary sinus unit and the right maxillary sinus unit being linked to the total maxillary sinus unit;
a left sphenoid sinus unit;
a right sphenoid sinus unit;
a total sphenoid sinus unit, the left sphenoid sinus unit and the right sphenoid sinus unit being linked to the total sphenoid sinus unit;
a cumulative sinus unit, the total frontal sinus unit, the total ethmoid sinus unit, the total maxillary sinus unit, and the total sphenoid sinus unit being linked to the cumulative sinus unit;
a left inferior turbinate unit;
a right inferior turbinate unit;
a total inferior turbinate unit, the left inferior turbinate unit and the right inferior turbinate unit being linked to the total inferior turbinate unit;
a left middle turbinate unit;
a right middle turbinate unit;
a total middle turbinate unit, the left middle turbinate unit and the right middle turbinate unit being linked to the total middle turbinate unit;

a cumulative turbinate unit, the total inferior turbinate unit and the total middle turbinate unit being linked to the cumulative turbinate unit;
a nasal valve unit;
a septum unit;
a nasal polyps unit;
a sinonasal total unit, the nasal valve unit, the septum unit, the nasal polyps unit, the cumulative sinus unit, and the cumulative turbinate unit being linked to the sinonasal total unit;
a tonsil unit, the sinonasal total unit being linked to the tonsil unit;
an adenoid unit;
an adenoid and PNS mass unit linked to the tonsil unit, the adenoid unit being linked to the adenoid and PNS mass unit;
an epiglottis unit;
a lateral pharyngeal wall unit;
a tongue base unit;
a cumulative tongue unit, the epiglottis unit, the lateral pharyngeal wall unit, and the tongue base unit being linked to the cumulative tongue unit, the cumulative tongue unit being linked to the adenoid and PNS mass unit; and
a soft palate unit linked to the cumulative tongue unit.

4. The method of evaluating the oral and nasal organs of a person having obstructive sleep apnea according to claim 3, wherein:
the total frontal sinus unit is assigned a value of zero or one;
the total ethmoid sinus unit is assigned a value of zero or one;
the total maxillary sinus unit is assigned a value of zero or one;
the total sphenoid sinus unit is assigned a value of zero or one;
the total inferior turbinate unit is assigned a value of zero or one;
the total middle turbinate unit is assigned a value of zero or one;
the nasal valve unit is assigned a value of zero or one;
the septum unit is assigned a value of zero or one;
the nasal polyps unit is assigned a value of zero or one;
the tonsil unit is assigned a value of zero or one;
the adenoid and PNS mass unit is assigned a value of zero or one;
the epiglottis unit is assigned a value of zero or one;
the lateral pharyngeal wall unit is assigned a value of zero or one;
the tongue base unit is assigned a value of zero or one;
the soft palate unit is assigned a value of zero or one; and
the values assigned to each of the units are added to provide a total score of between zero and fifteen, inclusive.

5. The method of evaluating the oral and nasal organs of a person having obstructive sleep apnea according to claim 1, further comprising the steps of:
(a) administering a medical history questionnaire to the person; and
(b) evaluating the results of the medical history questionnaire.

\* \* \* \* \*